United States Patent
Senturia et al.

(10) Patent No.: US 7,505,641 B1
(45) Date of Patent: Mar. 17, 2009

(54) OPTICAL BIOSENSOR INCORPORATING WAVELENGTH ENCODING OF MULTIPLE UNLABELED ANALYTES

(75) Inventors: Stephen D. Senturia, Brookline, MA (US); Malcolm C. Smith, Winchester, MA (US); Michael A. Butler, Winchester, MA (US); David R. Day, Boxford, MA (US)

(73) Assignee: Polychromix Corporation, Wilmington, MA (US)

( * ) Notice: Subject to any disclaimer, the term of this patent is extended or adjusted under 35 U.S.C. 154(b) by 0 days.

(21) Appl. No.: 11/505,636

(22) Filed: Aug. 17, 2006

Related U.S. Application Data

(60) Provisional application No. 60/708,973, filed on Aug. 17, 2005.

(51) Int. Cl.
*G02B 6/00* (2006.01)
*C12M 1/34* (2006.01)

(52) U.S. Cl. .................................... 385/12; 435/287.2
(58) Field of Classification Search .............. 435/287.2; 385/12
See application file for complete search history.

(56) References Cited

U.S. PATENT DOCUMENTS

| 2004/0145752 A1* | 7/2004 | Angeley ...................... 356/521 |
| 2004/0223881 A1* | 11/2004 | Cunningham et al. ..... 422/82.05 |
| 2005/0135723 A1* | 6/2005 | Carr et al. ...................... 385/12 |
| 2007/0196043 A1* | 8/2007 | Peled et al. ..................... 385/12 |

* cited by examiner

*Primary Examiner*—Charlie Peng
(74) *Attorney, Agent, or Firm*—Lowrie, Lando & Anastasi, LLP

(57) ABSTRACT

A waveguide-based sensor is disclosed that uses one or more grating patterns of a bioreceptor on a surface of the waveguide to provide a wavelength-specific sensor response without the requirement of labeling the target molecule or the bioreceptor. Furthermore, there is provided a biosensor that, at least to a first order, is insensitive to non-specific binding.

28 Claims, 4 Drawing Sheets

Type A grating

Type B grating

Type C grating

OPTICAL BIOSENSOR INCORPORATING WAVELENGTH ENCODING OF MULTIPLE UNLABELED ANALYTES

CROSS-REFERENCE TO RELATED APPLICATIONS

This application claims priority under 35 U.S.C. §119(e) to U.S. Provisional Application No. 60/708,973 filed Aug. 17, 2005, which is herein incorporated by reference in its entirety.

BACKGROUND

1. Field of the Invention

This invention relates to the use of optical techniques to permit the analysis of a biological or medical sample for the presence of multiple types of target molecules.

2. Discussion of Related Art

Biological assays that rely on pairs of bioreceptor-target molecules are well known, such as antibody-antigen reactions. Typically, one of the molecules is immobilized on a surface and a fluid sample containing the analyte is either applied to that surface or flowed over it through a suitable flow channel. The binding of the target to the bioreceptor, generally, produces an observable physical effect, such as a change in optical properties near the surface. Many of the most widely used assays rely on fluorescence changes when the target binds to the bioreceptor. This requires special molecular structure which, if not already present in the bioreceptor or the target, must be added by chemical means. Such addition is generally referred to as fluorescent labeling or 'tagging.'

It is generally desirable to be able to make simultaneous assays for multiple targets in a single sample. One common method of doing this is to create spatial arrays of bioreceptor regions in which each region of the array contains a different bioreceptor, each sensitive to a different target. Once the sample has interacted with the surface, imaging of the surface, for example, using fluorescence, then identifies which bioreceptor sites have changed their fluorescence, indicative of binding of the target. When using fluorescence, it is necessary to select the excitation wavelength so that fluorescence is excited and also to detect the emitted light at its appropriate wavelength.

SUMMARY OF THE INVENTION

Aspects and embodiments of the invention relate to the use of novel optical techniques to permit the analysis of a biological or medical sample for the presence of multiple types of target molecules. One embodiment may permit detection of multiple target species without requiring labeling. This detection may be accomplished, for example, with a range of optical wavelengths that can be chosen independent of any fluorescence or spectroscopic properties of the bioreceptor or target molecules. In another embodiment, a sensor may be provided that selects against non-specific binding of molecules to the device, whether in the form of the target molecule binding to sites that do not have the bioreceptor present, or other molecules binding indiscriminately to sites with or without the bioreceptor present.

Some aspects and embodiments may include a method for detecting the binding of a target to a bioreceptor that may include disposing the bioreceptor on the surface of a waveguide. The evanescent wave of light traveling in the waveguide may intercept the bioreceptor, thereby influencing the speed of light propagation in the waveguide through a parameter commonly referred to as the effective index. When a target molecule becomes attached to the bioreceptor, the evanescent wave may be further perturbed, producing a change in the effective index. One method for detecting changes in effective index is to build a Mach-Zender interferometer using waveguides and to apply the bioreceptor to only one arm of the interferometer. The phase change in the sensing arm produced by small changes in effective index created by the binding of target molecules can be sensed in a change in the output of the interferometer. However, such a structure can only detect one species per interferometer. Hence, one embodiment of the present invention may permit the compact and efficient detection of multiple unlabeled species with compact optical devices.

According to one embodiment, a biosensor may be adapted to detect unlabelled target species. The biosensor may comprise a waveguide and a grating disposed on a surface of the waveguide, the grating comprising a bioreceptor located on a surface of the grating.

According to another embodiment, there is provided a method of detecting a target species using a biosensor comprising a first grating formed of a first bioreceptor and having a first periodicity, the first grating being disposed on a surface of the waveguide. The method comprises steps of providing an evanescent signal in the waveguide, providing a medium on the waveguide, the medium containing a first target species adapted to bind to the first bioreceptor, receiving a back-reflection of the evanescent signal produced by the first grating, and determining a presence of the first target species based on a magnitude and a wavelength of the back-reflection, a greater magnitude of the back-reflection corresponding to a greater presence of the first target species.

Another embodiment is directed to a biosensor adapted to detect a target species while being insensitive to non-specific binding. The biosensor comprises a waveguide, and a first bioreceptor disposed in a diffractive pattern with a first periodicity on a surface of the waveguide and adapted to bind to a first target species, wherein the first bioreceptor is adapted to cause a first back-reflection of a evanescent signal in the waveguide, the first back-reflection having a first wavelength based on the first periodicity, and a first signal strength dependent on whether the first target species is bound to the first bioreceptor, and wherein the first signal strength of the first back-reflection is unaffected by non-specific binding of a non-target species to both the first bioreceptor and the surface of the waveguide.

According to another embodiment, there is provided a method of manufacture of a biosensor capable of detecting an unlabelled target species, the method comprising steps of providing a waveguide, and forming a grating comprising a bioreceptor disposed on a surface of the grating on a surface of the waveguide.

DETAILED DESCRIPTION

Figure 1:
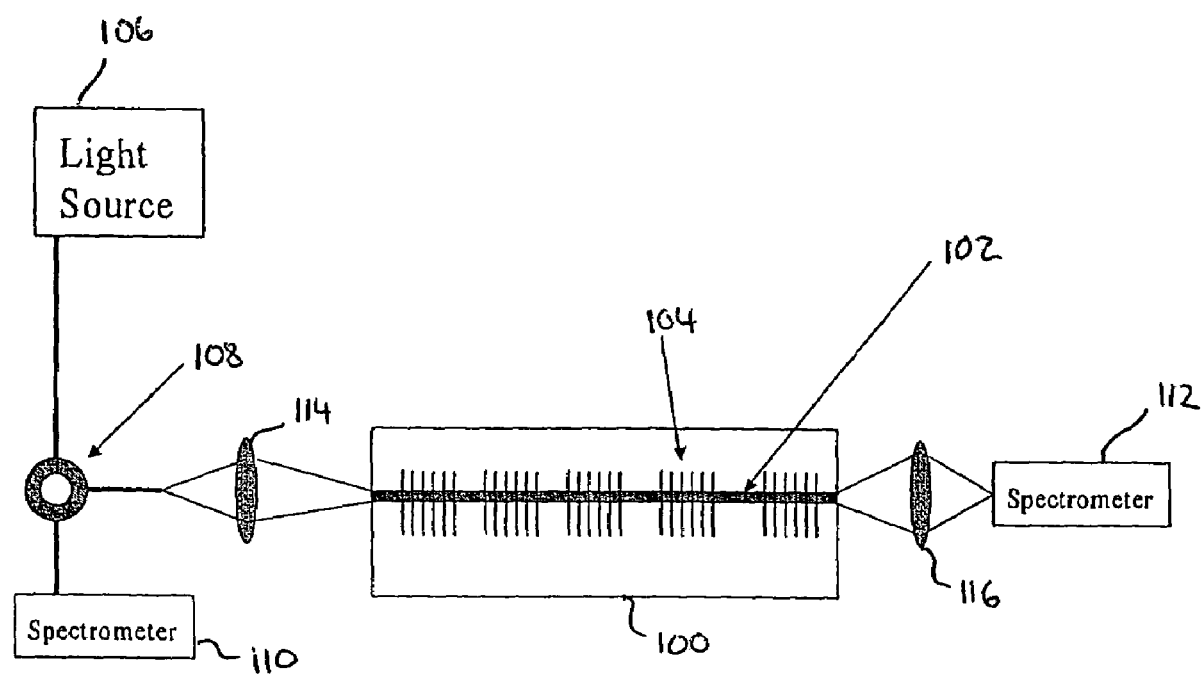
FIG. 1 is a block diagram of one embodiment of a biosensor system according to aspects of the invention.

Various illustrative embodiments and aspects thereof will now be described in detail with reference to the accompanying figures. It is to be appreciated that this invention is not limited in its application to the details of construction and the arrangement of components set forth in the following description or illustrated in the drawings. The invention is capable of other embodiments and of being practiced or of being carried out in various ways. Examples of specific implementations are provided herein for illustrative purposes only and are not intended to be limiting. In particular, acts, elements and features discussed in connection with one embodiment are not intended to be excluded from a similar role in other embodiments. Also, the phraseology and terminology used herein is for the purpose of description and should not be regarded as limiting. The use of "including," "comprising," "having," "containing," "involving," and variations thereof herein, is meant to encompass the items listed thereafter and equivalents thereof as well as additional items.

According to various aspects and embodiments of the invention, a biosensor may incorporate a grating, for example, a Bragg grating, disposed on one or more surfaces of an optical waveguide such that the grating is located within a portion of the evanescent wave of the waveguide. The grating, which may incorporate the bioreceptor on its surface, is comprised of a pattern of fine lines whose spacing is controlled to be comparable to the wavelength of light in the waveguide. For example, if the light in the waveguide has a free-space wavelength of 1.5 microns, the pattern of lines and spaces of the bioreceptor may have a periodicity on the order of 0.75 microns, with the exact spacing determined by a more precise set of design constraints explained below.

Referring to FIG. 1, there is illustrated one example of a system incorporating a biosensor according to embodiments of the invention. The system includes a biosensor chip 100 that comprises a waveguide 102 and one or more gratings 104 disposed on a surface of the waveguide 102. The system further includes a light source 106 that provides an optical signal to interrogate the sensor chip 100, as well as spectrometers 110 and 112 to measure reflected and/or transmitted light from the sensor chip. In one example, a circulator 108 and signal coupling devices 114 and 116 may also be provided. However, it is to be appreciated that these elements are not required.

According to one embodiment, the presence of a Bragg grating on the surface of the waveguide creates a periodic modulation of the effective index of light propagating in the waveguide. This will be true whether the grating is produced by actually etching a relief pattern into a thin dielectric layer on the surface of the waveguide (conventionally referred to as the cladding), or is produced by depositing lines of bioreceptor, together with any molecular species or adhesion promoter that might be required to adhere the bioreceptor to the waveguide surface or to the surface of a cladding that may be present. The strength of this modulation increases when target molecules bind to the bioreceptor, but, to first order, the strength of this modulation does not change if molecules bind non-specifically to both lines comprised of bioreceptor and spaces without bioreceptor. Hence, the Bragg-grating structure is intrinsically insensitive to non-specific binding.

For a given periodicity of lines and spaces, the presence of the Bragg grating will induce a back-reflection of light propagating in the waveguide only at a wavelength that meets the following phase-matching condition:

$$\lambda_{Bragg} = 2\Lambda n_0$$

where $\Lambda$ is the spatial period of the grating and $n_e$ is the effective index of the propagating wave. This will be true even when the Bragg-grating-coated waveguide is immersed in water or some other fluid as long as the bioreceptor, and any molecule binding to the bioreceptor, has an index of refraction that differs from that of the bounding fluid, a situation that is typical of such materials.

The strength of the back-reflection depends on the thickness of the bioreceptor coating through the dependence of the depth of modulation of the effective index upon coating thickness. When a target molecule binds to the bioreceptor, replacing a thin layer of the water with additional biological molecules, the strength of the back-reflection increases according to the following formula:

$$R = \left|\tanh\left(\frac{\Delta n_{max}}{2\beta/\kappa}\kappa L\right)\right|^2$$

where $\Delta n_{max}$ is the maximum effective index modulation due to the biological grating, $\beta$ is the waveguide propagation constant, $\kappa = 2\pi/\lambda$, $\lambda$ is the free-space wavelength of the light in the waveguide, and L is the grating length. Therefore, it is possible, using a single Bragg reflector disposed at the surface of an optical waveguide such that it intercepts the evanescent field of the waveguide to reflect light of a specific wavelength propagating in the waveguide with a strength that depends on the presence or absence of the binding of target molecules to the bioreceptor.

Figure 2:
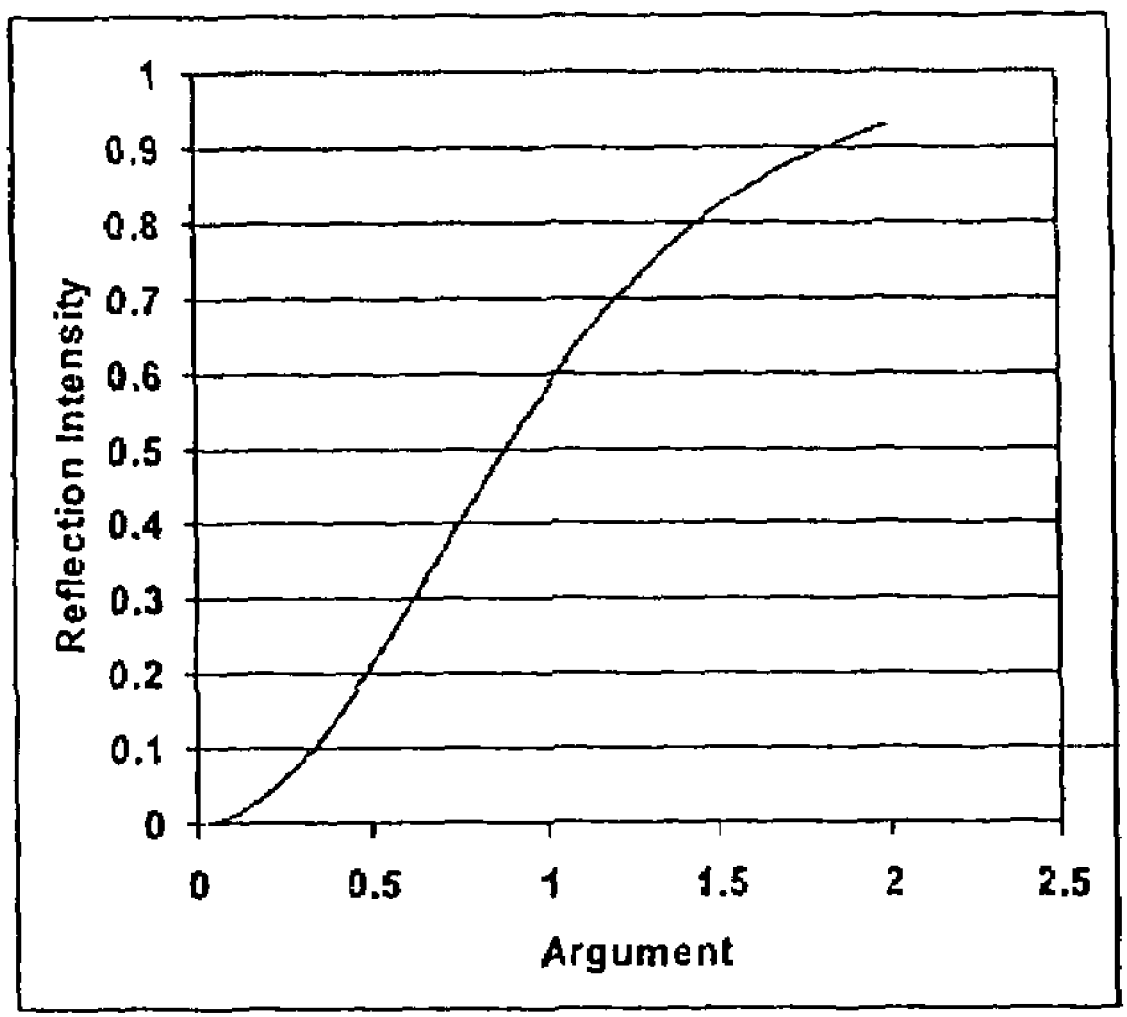
FIG. 2 is a graph of the strength of a back-reflected signal versus an index proportional to the amount of bound target molecule.

A plot of R versus the argument of the hyperbolic tangent is shown in FIG. 2. The argument is proportional to the change in effective index modulation and thus the amount of adsorbed target molecule plus any effective index modulation or "bias" due to the bio-receptor grating structure. As long as the total height of the grating structure is less than the decay length of the evanescent field, the change in effective index is quite linear with adsorbed target molecule layer thickness.

The biosensor's sensitivity to adsorbed target molecules is determined by the slope of the reflectivity versus argument curve. Since this curve is quadratic as the argument tends to zero, the sensitivity to the adsorbed target molecule will also tend to zero. This poor sensitivity at low adsorbed species coverage can be overcome by "biasing" the grating into the linear region or a reflectivity of about 0.5. This biasing can be achieved with grating structures of the type A and C shown in FIGS. 3 and 5, respectively.

Because the wavelength at which the back reflection occurs depends only on the periodicity of the Bragg grating, it is possible to dispose a series of Bragg gratings with slightly different periods on the surface of a single waveguide, as shown in FIG. 1. Provided that each grating is formed with a different bioreceptor, then such a waveguide will experience back-reflections at a multiplicity of wavelengths, each wavelength corresponding to one and only one of the bioreceptors. Thus, an encoding of the binding of a specific target molecule to a change in the back-reflected intensity at a correspondingly specific wavelength is achieved, without the requirement of fluorescent labeling. Simple spectroscopic analysis of the back-reflected (or transmitted) light is sufficient to identify how much of each target species is bound to its corresponding bioreceptor. Furthermore, the requirement of binding of the target molecule to the bioreceptor in the grating pattern for there to be a change in light transmission at a specific wavelength, means that the sensor will not respond to non-specific binding where the target or other molecules bind uniformly over the waveguide surface.

Another use for an array of gratings with different spatial frequencies may be achieved if all the gratings are made with the same bioreceptor. Since the grating length and effective index occur as a product in the expression for back reflection intensity, by varying the length as well as the spatial frequency of the gratings the range of sensitivity of the biosensor can be extended over several orders of magnitude.

Fabrication methods for planar or rib waveguides are well known, as is the physics governing the extension of the evanescent wave of light in a waveguide into the surrounding medium. There are several methods that can be used to achieve the goal of defining a Bragg grating (comprised at its outer surface of a bioreceptor) on at least one surface of the waveguide. One method is to use conventional lithography, for example, with lift-off techniques, to bind a bioreceptor to the waveguide surface. This may require the use of a coupling agent, such as a self-assembled monolayer surfactant, to promote adhesion of the bioreceptor to the waveguide surface. Alternatively, one can print the bioreceptor directly onto the surface using the method of soft lithography. A fine-line mold, with the required line-and-space periodicity is formed in a substrate such as a silicon wafer by reactive-ion etching or similar means; the relief pattern is then replicated in a soft material such as poly-methyldisiloxane (PMDS) using conventional molding techniques. The PMDS is then dipped into a solution containing the bioreceptor and subsequently pressed onto the waveguide surface, transferring a line-and-space pattern of bioreceptor to the waveguide surface. This process can be repeated with different molds having slightly different periodicities so that a multiplicity of Bragg gratings is created along a single waveguide. In one embodiment, each Bragg grating can be formed with a different bioreceptor such that binding of a target to a bioreceptor produces enhanced back-reflection (reduced transmission) at a specific wavelength of light linked to the specific periodicity of that bioreceptor's Bragg grating.

Figure 3:
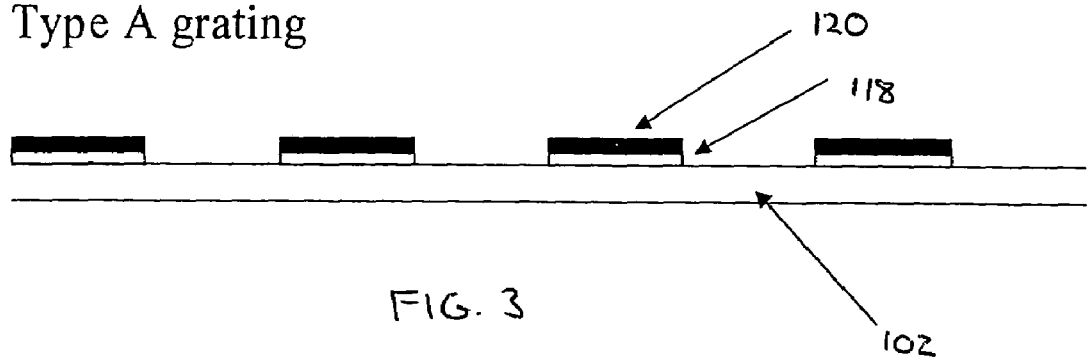
FIG. 3 is a diagram of one example of a grating that may be used in a biosensor according to aspects of the invention.

The above two methods produce a grating type referred to as a type A grating and illustrated in FIG. 3. Referring to FIG. 3, the white rectangles 118 are the active bioreceptor layer and the black rectangles 120 are the bound target molecule. The waveguide 102 runs perpendicular to the grating lines, as shown in FIG. 3. The length of the grating may be chosen to give a reflectivity bias of 0.5 from the active bio-receptor layer grating alone.

Figure 4:
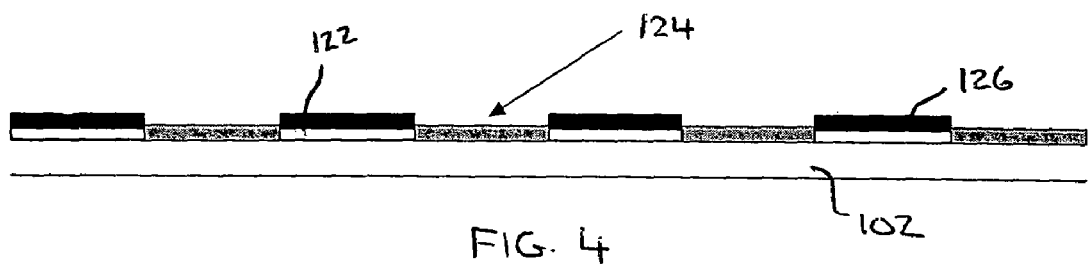
FIG. 4 is a diagram of another example of a grating.

A third method of manufacture that may be used to form a Bragg grating in accordance with the invention is described in the paper by Tsay et al. titled "Optical Biosensor Assay," published in *Clin. Chem.* 37/9 1502-1505 (1991), which is herein incorporated by reference. Using this method, The bioreceptor is uniformly distributed on the substrate and then exposed to UV through a grating mask. With proper exposure levels the UV de-activates the bioreceptor in the exposed regions so that it will not bind the target molecule. When the sensing chip is exposed to the target molecule a grating pattern is generated on the substrate. An advantage of this method is that without exposure to the target molecule there is little grating structure and little influence on the light passing through the waveguide. This method of forming a grating leads to a type B grating illustrated in FIG. 4. Referring to FIG. 4, the white rectangles 122 are active bio-receptor layer, the gray rectangles 124 are bio-receptor layer deactivated by exposure to UV, and black rectangles 126 are the adsorbed target molecules. The reflectivity bias from the differences in the active and deactivated bio-receptor layer may be quite small and this type of grating will not be optimum for applications requiring maximum sensitivity.

Figure 5:
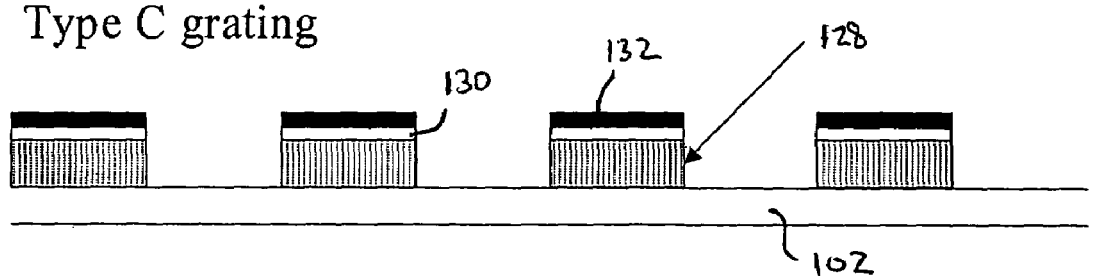
FIG. 5 is a diagram of another example of a grating.

A third type of grating, referred to as a type C grating and illustrated in FIG. 5 may be formed by etching a bias grating into the cladding of the desired period with the grooves of the desired depth. The bias grating is illustrated as the gray rectangles 128. While FIG. 5 shows this bias grating as being etched through the full thickness of the cladding, it is also possible to etch through only a portion of the cladding, leaving some cladding present on the waveguide surface in the spaces between the grating lines. The ridges in the grating are coated with an active bio-receptor layer using, for example, a printing method similar to that used above. The active bio-receptor layer is represented by the white rectangles 130. The target molecules then bind to the bio-receptor layer, shown as the black rectangles 132. An advantage of this structure is the added ability to adjust the reflectivity bias by varying the groove depth of the initial grating structure, which will allow a considerably shorter grating for optimum sensitivity. Other grating structures, such as etching the bias grating into the surface of the waveguide itself, and other methods of grating formation and bioreceptor deposition are possible and are included in this invention.

Figure 6:
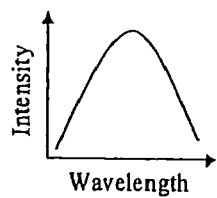
FIG. 6 is a plot of one example of a light spectrum that may be used in an optical biosensor system according to an embodiment of the invention.
Figure 7:
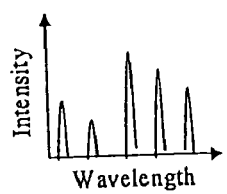
FIG. 7 is a plot of one example of a reflected light spectrum from the system of FIG. 1 stimulated with the light spectrum illustrated in FIG. 6.
Figure 8:
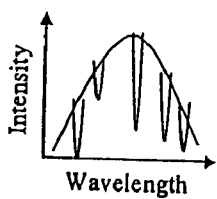
FIG. 8 is a plot of one example of a transmitted light spectrum from the system of FIG. 1 stimulated with the light spectrum illustrated in FIG. 6.

The biosensor can be used either in air, where the sensing chip has been exposed to the test sample containing the target molecules and then washed and dried, or in solution where the test sample is flowed across the biosensor to expose it. Higher sensitivity is achieved when interrogating the biosensor in air. Interrogation of the biosensor requires light of suitable wavelength to be coupled into the waveguide using any one of several well-known methods; such as butt coupling, prism coupling, and grating coupling. The light may be provided by any light source at any wavelength from UV to the mid infrared, but preferably from an LED operating in the telecom c-band, approximately, 1530-1570 nm. Referring again to FIG. 1, the light source 106 is shown coupled to the sensor chip 100 via a circulator 108 and a coupling device 114. However, it is to be appreciated that the invention does not require the use of these elements. One example of a light signal that may be provided by the light source 106 is illustrated in FIG. 6 as a plot of the light intensity versus wavelength. It may be important that the period of the grating 104 be appropriate for the wavelength of light used. The LED provides a strong light source over the whole C-band and enables measurement of the spectral response of the sensor utilizing technology developed for optical telecom applications. This provides a measurement of all the different grating structures deposited on the waveguide and thus an array of bioreceptors, at the same time. Technology, developed for telecom applications, uses UV light to form Bragg grating structures in optical fibers. This technology can be adapted following the paper by Tsay et al to form the grating structure from the bioreceptor on the sensing chip, as discussed above. The response of the biosensor to exposure to the target molecule is to reduce transmission of the light at the specific wavelength determined by the grating period. This light is reflected back along the waveguide in the direction from which the light came. Thus sensor response can be measured by looking at either the enhancement of the back-reflected light at the specific wavelength, the reduction in transmission of light at that wavelength, or by differential comparison of the reflected and transmitted light. For example, referring to FIG. 1, the reflected light may be measured using a spectrometer 110 and/or the transmitted light may be measured using another spectrometer 112. FIG. 7 illustrates one example of a reflected light spectrum that may be observed at spectrometer 110 corresponding to the input light spectrum illustrated in FIG. 6. FIG. 8 illustrates one example of a transmitted light spectrum that may be observed at spectrometer 112 corresponding to the input light spectrum illustrated in FIG. 6. For the back-reflected light a means must be provided for separating the back-reflected light from the in-coupled light, for example, with a fiber-optic circulator. The biosensor is self-referencing in that the grating structures have no effect at wavelengths other than those for which they were designed. Thus light intensity fluctuations and fiber-coupling variations can easily be monitored at wavelengths where there is no grating.

Having thus described several aspects of at least one embodiment of this invention, it is to be appreciated various alterations, modifications, and improvements may readily occur to those skilled in the art. Such and alterations, modifications, and improvements are intended to be part of this disclosure and are intended to be within the scope of the invention. Accordingly, the foregoing description and drawings are by way of example only and the scope of the invention should be determined from proper construction of the appended claims, and their equivalents.

What is claimed is:

1. A biosensor adapted to detect unlabelled target species, the biosensor comprising:
    a waveguide; and
    a grating disposed on a planar surface of the waveguide, the grating comprising a series of lines of active bioreceptor deposited on the planar surface of the waveguide and spaced apart from one another by a corresponding series of spaces such that the grating has a first periodicity;
    wherein a height of the grating is less than a decay length of an evanescent field formed by a signal propagating in the waveguide.

2. The biosensor of claim 1, wherein the waveguide has an operating frequency range, and wherein the first periodicity of the grating is selected depending on the operating frequency range of the waveguide.

3. The biosensor of claim 1, further comprising at least one additional grating disposed on the planar surface of the waveguide; wherein the at least one additional grating has a second periodicity different than the first periodicity and comprises an additional, different bioreceptor.

4. The biosensor of claim 1, wherein the biosensor operates at an optical detection wavelength that is based at least in part on a periodicity of the grating and is independent of any fluorescence or spectroscopic properties of the bioreceptor.

5. A biosensor adapted to detect unlabelled target species, the biosensor comprising:
    a waveguide; and
    a grating disposed on a surface of the waveguide, the grating comprising a bioreceptor located on a surface of the grating;
    wherein a height of the grating is less than a decay length of an evanescent field formed by a signal propagating in the waveguide.

6. The biosensor of claim 5, wherein the grating is a Bragg grating.

7. The biosensor of claim 5, further comprising multiple gratings disposed on the surface of the waveguide, each grating comprising the bioreceptor disposed on a surface of each grating, and wherein each of the multiple gratings comprises a series of lines spaced apart from one another by a given spacing that is different for each grating of the multiple gratings, such that each grating on the waveguide has a different periodicity to each other grating so as to extend a sensitivity of the biosensor.

8. The biosensor of claim 5, wherein the grating comprises a series of lines of active bioreceptor adhered to the surface of the waveguide and separated from one another by a series of spaces, such that the grating has a defined periodicity.

9. The biosensor of claim 8, further comprising a coupling agent that promotes adhesion of the bioreceptor to the surface of the waveguide.

10. The biosensor of claim 5, wherein the grating comprises a series of alternating lines of active bioreceptor and inactive bioreceptor adhered to the surface of the waveguide.

11. The biosensor of claim 5, wherein the waveguide comprises a cladding layer on the surface of the waveguide and wherein the grating comprises:
    a bias grating including a series of alternating protrusions and grooves formed by etching of the cladding layer; and
    the bioreceptor disposed on a surface of each of the protrusions of the bias grating.

12. A system comprising:
    the biosensor of claim 5;
    a light source coupled to the waveguide and constructed and arranged to provide the signal propagating in the waveguide;
    a spectrometer coupled to the light source and to the waveguide and adapted to analyze a back-reflection produced by the grating.

13. A biosensor adapted to detect unlabelled target species, the biosensor comprising:
    a waveguide;
    a grating disposed on a surface of the waveguide, the grating comprising a series of lines of bioreceptor adhered to a surface of the waveguide and separated from one another by a series of spaces, such that the grating has a defined periodicity; and
    a coupling agent that promotes adhesion of the bioreceptor to the surface of the waveguide;
    wherein the coupling agent is a self-assembled monolayer surfactant.

14. The biosensor of claim 13, further comprising multiple additional gratings disposed on at least one surface of the waveguide, each of the multiple additional gratings comprising the bioreceptor and having a different predetermined periodicity.

15. A system comprising:
    the biosensor of claim 13;
    a light source coupled to the waveguide and adapted to provide an evanescent signal propagating in the waveguide;
    a spectrometer coupled to the light source and to the waveguide and adapted to analyze a back-reflection produced by the grating.

16. A biosensor adapted to detect a target species while being insensitive to non-specific binding, the biosensor comprising:
    a waveguide; and
    a first bioreceptor disposed in a diffractive pattern with a first periodicity on a surface of the waveguide and constructed and arranged to bind to a first target species;
    wherein the first bioreceptor is constructed and arranged to cause a first back-reflection of a evanescent signal in the waveguide, the first back-reflection having a first wavelength based on the first periodicity, and a first signal strength dependent on whether the first target species is bound to the first bioreceptor; and wherein the first bioreceptor is constructed and arranged to cause the first signal strength of the first back-reflection to be unaffected by non-specific binding of a non-target species to both the first bioreceptor and the surface of the waveguide.

17. The biosensor of claim 16, further adapted to detect multiple target species and further comprising:

a second bioreceptor disposed in a diffractive pattern with a second periodicity on the surface of the waveguide;

wherein the second bioreceptor is constructed and arranged to cause a second back-reflection of the evanescent signal in the waveguide, the second back-reflection having a second wavelength based on the second periodicity, and a second signal strength dependent on whether the second target species is bound to the second bioreceptor; and wherein the first and second back-reflections are unaffected by non-specific binding of a non-target species to all of the first bioreceptor, the second bioreceptor and the surface of the waveguide.

18. A biosensor constructed and arranged to detect unlabelled target species, the biosensor comprising:

a waveguide having a surface; and a bioreceptor adhered to the surface of the waveguide, the bioreceptor being disposed in a series of lines separated from one another by a corresponding series of spaces to provide a grating with a first periodicity;

wherein a height of the grating is less than a decay length of an evanescent field formed by a signal propagating in the waveguide.

19. The biosensor of claim 18, further comprising:

a cladding layer disposed on the surface of the waveguide; and a bias grating etched into the cladding layer, the bias grating comprising a series of alternating protrusions and grooves;

wherein the bioreceptor is disposed on a top surface of each of the protrusions of the bias grating.

20. The biosensor of claim 18, further comprising a coupling agent that binds the bioreceptor to the surface of the waveguide.

21. The biosensor of claim 20; wherein the coupling agent is a self-assembled monolayer surfactant.

22. The biosensor of claim 18, wherein the bioreceptor is disposed in multiple series of lines to provide multiple gratings; and wherein each of the multiple gratings has a different periodicity.

23. The biosensor of claim 18, further comprising a second bioreceptor adhered to the surface of the waveguide to provide a second grating with a second periodicity.

24. The biosensor of claim 23, wherein the second periodicity is different than the first periodicity.

25. A biosensor comprising:

a waveguide having a surface; and a bioreceptor layer disposed on the surface of the waveguide;

wherein the bioreceptor layer is patterned to provide at least one grating; and wherein the bioreceptor layer comprises at least one bioreceptor;

wherein a height of the at least one grating is less than a decay length of an evanescent field formed by a signal propagating in the waveguide.

26. The biosensor of claim 25, wherein the bioreceptor layer comprises a first grating having a first periodicity and a second grating having a second periodicity.

27. The biosensor of claim 26, wherein the bioreceptor layer comprises a first bioreceptor forming the first grating and a second bioreceptor forming the second grating.

28. A system comprising:

a biosensor including a waveguide and a bioreceptor deposited on a surface of the waveguide and arranged in a series of lines separated by a corresponding series of spaces to form a grating with a first periodicity;

a light source coupled to the waveguide and adapted to provide an evanescent signal propagating in the waveguide; and a spectrometer coupled to the light source and to the waveguide and adapted to analyze a back-reflection produced by the grating;

wherein a height of the grating is less than a decay length of an evanescent field formed by the evanescent signal propagating in the waveguide.

* * * * *